(12) United States Patent
Fujisawa (10) Patent No.: US 7,697,740 B2
(45) Date of Patent: Apr. 13, 2010

(54) MEDICAL IMAGE PROCESSING SYSTEM AND MEDICAL IMAGE PROCESSING METHOD

(75) Inventor: Yasuko Fujisawa, Otawara (JP)

(73) Assignees: Kabushiki Kaisha TOshiba, Tokyo (JP); Toshiba Medical Systems Corporation, Otawara (JP)

( * ) Notice: Subject to any disclaimer, the term of this patent is extended or adjusted under 35 U.S.C. 154(b) by 845 days.

(21) Appl. No.: 11/551,474

(22) Filed: Oct. 20, 2006

(65) Prior Publication Data
US 2007/0092067 A1 Apr. 26, 2007

(30) Foreign Application Priority Data
Oct. 21, 2005 (JP) .............................. 2005-307836

(51) Int. Cl.
*G06K 9/00* (2006.01)
*H05G 1/10* (2006.01)
(52) U.S. Cl. ........................... 382/128; 382/153; 378/95
(58) Field of Classification Search ................. 382/100, 382/128, 129, 130, 131, 132, 133, 134, 168, 382/181, 190–197, 199, 203, 232, 256, 274, 382/276, 285–297, 305, 312; 378/196, 98.12, 378/62, 95; 600/410; 345/419
See application file for complete search history.

(56) References Cited
U.S. PATENT DOCUMENTS
6,508,586 B2 * 1/2003 Oota .......................... 378/196

7,283,614 B2 * 10/2007 Nakano et al. ........... 378/98.12
7,340,033 B2 * 3/2008 Mollus et al. .................. 378/62
7,424,140 B2 * 9/2008 Matsumoto .................. 382/128
7,432,924 B2 * 10/2008 Ohishi ......................... 345/419
7,450,982 B2 * 11/2008 Abe et al. .................... 600/410
7,496,175 B2 * 2/2009 Sakaguchi et al. ............. 378/95

FOREIGN PATENT DOCUMENTS
JP 2002-102220 4/2002

* cited by examiner

*Primary Examiner*—Seyed Azarian
(74) *Attorney, Agent, or Firm*—Oblon, Spivak, McClelland, Maier & Neustadt, L.L.P.

(57) ABSTRACT

IVR-CT apparatus has an angio-image obtaining unit, an angio-image imaging direction obtaining unit, a CT-image obtaining unit, a blood vessel part extracting unit, a projected image generating unit and a display control unit. The angio-image obtaining unit obtains a required angio-image from multiple chronological angio-images. The angio-image imaging direction obtaining unit obtains a direction of imaging as incidental information included in data on the required angio-image. The CT-image obtaining unit obtains a three-dimensional CT-image corresponding to the required angio-image. The blood vessel part extracting unit extracts a blood vessel part in the three-dimensional CT-image. The projected image generating unit generates a three-dimensional projected image by projecting the blood vessel part, and a three-dimensional projected image corresponding to a direction of a projection after a manual operation operates the direction of the projection. The display control unit makes display the three-dimensional projection image and the angio-image one over another.

22 Claims, 8 Drawing Sheets

MEDICAL IMAGE PROCESSING SYSTEM AND MEDICAL IMAGE PROCESSING METHOD

BACKGROUND OF THE INVENTION

1. Field of the Invention

The present invention relates to a technology for displaying a computerized tomography (CT) image and, in particular, to a medical image processing system and method for evaluating the rate of a narrowing of a coronary and/or a characteristic of a blood vessel by defining a plane to project a CT-image to be displayed.

2. Description of the Related Art

An interventional Radiology-computerized tomography (IVR-CT) apparatus has been proposed which has a combination of an X-ray CT apparatus and a radiographic X-ray apparatus including a C-arm, which is a substantially C-shaped supporting device.

The X-ray CT apparatus includes a CT base (gantry) having a hollow part around which an X-ray generating source and an X-ray detector are provided. A subject (patient) mounted on a table-top is introduced into the hollow part, and X-ray transmission information (projection data) in directions on the subject is by rotating the X-ray generating source and the X-ray detector around the hollow part. Based on the information, a tomographic image is reconstructed.

On the other hand, the radiographic X-ray apparatus performs radiographic X-ray by using an X-ray generating source at one end of the C-arm and an image intensifier (I.I.) functioning as an X-ray detecting device at the other end. In particular, the radiographic X-ray apparatus is used for the purposes of angiography within the subject. This is also generally called an angio apparatus. The angio apparatus allows the simultaneous implementation of the operation of insertion of a catheter into (that is, operation or examination by a doctor on) a subject and radiographic X-ray in parallel.

The IVR-CT apparatus allows the operation or positioning of the CT gantry in the X-ray CT apparatus and the C-arm in the angio apparatus provided in parallel within one space. For example, based on information on the subject, which is obtained by one apparatus, how an examination is to be performed in the other apparatus may be determined, and the examination may be carried out after a shorter period of time.

Currently, a visual blood vessel evaluations are performed based on a curved multi planer reconstruction (CPR) image, a minor axis image (horizontal section image) or a volume rendering (VR) image along blood vessel ramifications (blood vessel lining membrane) extracted from CT reconstruction data. The display of an image projecting a curved plane included in a blood vessel lining membrane has been proposed as display allowing the easy diagnosis, which is closer to the senses of an observer. For the diagnosis of the heart, the image display may be more effective with the display in the same direction of the projection (direction of vision of an observer) as the imaging direction in the coronary angiography.

In order to perform the evaluation on a characteristic of blood vessels such as the evaluation of the rate of a narrowing on a CT-image, the display of the CT-image in the same direction of the projection (direction of vision of an observer) as the direction of imaging of an angio-image thereof is effective. However, the strict reproduction of the same direction of the projection as the direction of the imaging of the angio-image on the CT-image is difficult because of the difference in modality or since the generation of CT-images in the same heartbeat phase timing as that of angio-images is difficult.

An optimum direction of imaging of the angio-image is defined by irradiating X-rays to a subject in the operation of a percutaneous coronary intervention (PCI), which is a method for extending a coronary narrowed by arteriosclerosis by using a catheter. However, the definition (search) of the direction of imaging of the angio-image takes time, and a subject may be exposed to X-rays, which is a problem. The amount of exposure to X-rays is desirably reduced by defining the disease part and an optimum direction of imaging of the angio-image by using a pre-shot CT-image. However, the reproduction of the direction of imaging of the angio-image in coronary angiography from the direction of display of the CT-image is difficult unless the projected image of the target vessel is only used.

SUMMARY OF THE INVENTION

The present invention has taken into consideration the above-described problems, and it is an object of the present invention to provide a medical image processing system and a medical image processing method such that same direction of a projection as a direction of imaging of an angio-image can be reproduced on a three-dimensional CT-image.

In addition, the present invention has taken into consideration the above-described problems, and it is an object of the present invention to provide a medical image processing system and a medical image processing method such that a characteristic of blood vessels such as the evaluation of the rate of a narrowing can be evaluated more accurately by displaying a CT curved-planer projected image in the same direction of a projection as a direction of imaging of a angio-image.

In addition, the present invention has taken into consideration the above-described problems, and it is an object of the present invention to provide a medical image processing system and a medical image processing method such that PCI can be performed in a shorter operation time and with a smaller amount of exposure to a subject.

To solve the above-described problems, the present invention provides the medical image processing system to mention it in a claim 1, comprising: an angio-image obtaining unit for obtaining a required angio-image from multiple chronological angio-images; an angio-image imaging direction obtaining unit for obtaining a direction of imaging as incidental information included in data on the required angio-image; a CT-image obtaining unit for obtaining a three-dimensional CT-image corresponding to the required angio-image; a blood vessel part extracting unit for extracting a blood vessel part in the three-dimensional CT-image; a projected image generating unit for generating a three-dimensional projected image by projecting the blood vessel part, and for generating a three-dimensional projected image corresponding to a direction of a projection after a manual operation operates the direction of the projection; and a display control unit for making display the three-dimensional projected image and the angio-image.

To solve the above-described problems, the present invention provides the medical image processing system to mention it in a claim 7, comprising: an angio-image obtaining unit for obtaining a required angio-image from multiple chronological angio-images; an angio-image imaging direction obtaining unit for obtaining a direction of imaging as incidental information included in data on the required angio-image; a CT-image obtaining unit for obtaining a three-dimensional CT-image corresponding to the required angio-image; a blood vessel part extracting unit for extracting a blood vessel part in the three-dimensional CT-image; a direction of projection defining unit for defining a direction of a projection; a projected image generating unit for generating a three-dimensional projected image by projecting the blood vessel part in the direction of the projection; an angiogram extracting unit for extracting an angiogram contained in the required angio-image; and a display control unit for making display the three-dimensional projected image and the angiogram, wherein the direction of projection defining unit defines the direction of the projection of the three-dimensional projected image corresponding to the direction of imaging of the required angio-image, by comparing the blood vessel part and the angiogram.

To solve the above-described problems, the present invention provides the medical image processing system to mention it in a claim 16, comprising: an angio-image obtaining unit for obtaining a required angio-image from multiple chronological angio-images; an angio-image imaging direction obtaining unit for obtaining a direction of imaging as incidental information included in data on the required angio-image; a CT-image obtaining unit for obtaining a three-dimensional CT-image corresponding to the required angio-image; a blood vessel part extracting unit for extracting a blood vessel part in the three-dimensional CT-image; a projected image generating unit for generating a three-dimensional projected image by projected the blood vessel part, and for generating a three-dimensional projected image corresponding to a direction of a projection after a manual operation operates the direction of the projection; a display control unit for making display the three-dimensional projection image and the angio-image; and a direction-of-vision correspondence information generating unit for generating a direction-of-vision correspondence information including a correspondence established between the direction of the projection after it was changed based on the manual operation and the direction of imaging, wherein a position of a C-arm on an angio apparatus be controlled so as to obtain a direction of imaging corresponding to the direction of the projection after it was changed based on the manual operation.

To solve the above-described problems, the present invention provides the medical image processing method to mention it in a claim 22, comprising steps of: obtaining a required angio-image from multiple chronological angio-images; obtaining a direction of imaging as incidental information included in data on the required angio-image; obtaining a three-dimensional CT-image corresponding to the required angio-image; extracting a blood vessel part in the three-dimensional CT-image; generating a three-dimensional projected image by projecting the blood vessel part; having display the three-dimensional projected image and the required angio-image; and generating direction-of-vision correspondence information including a correspondence of the mutual directions of vision between a direction of a projection after it was changed and the direction of imaging.

Therefore, according to the present invention to provide a medical image processing system and a medical image processing method, same direction of a projection as a direction of imaging of an angio-image can be reproduced on a three-dimensional CT-image.

In addition, according to the present invention to provide a medical image processing system and a medical image processing method, a characteristic of blood vessels such as the evaluation of the rate of a narrowing can be evaluated more accurately by displaying a CT curved-planer projected image in the same direction of a projection as a direction of imaging of a angio-image.

In addition, according to the present invention to provide a medical image processing system and a medical image processing method, PCI can be performed in a shorter operation time and with a smaller amount of exposure to a subject.

DESCRIPTION OF THE PREFERRED EMBODIMENTS

With reference to the attached drawings, embodiments of a medical image processing system and a medical image processing method according to the invention will be described.

Figure 1:
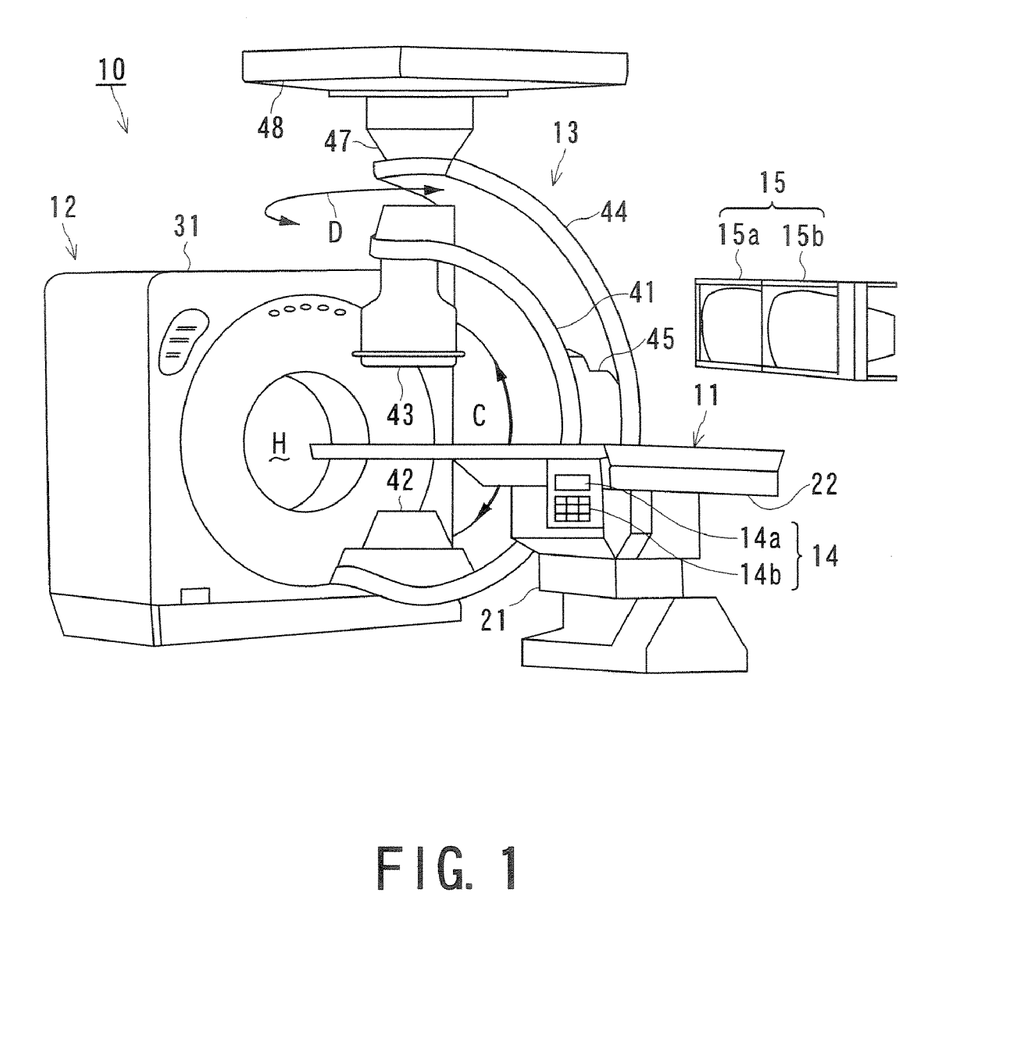
FIG. 1 is a schematic diagram showing an entire construction of an IVR-CT apparatus including a medical image processing system according to the invention.

FIG. 1 is a schematic diagram showing an entire construction of an interventional radiology-computerized tomography (IVR-CT) apparatus including a medical image processing system according to the invention.

FIG. 1 shows an IVR-CT apparatus 10 including a CT gantry in an X-ray CT apparatus and a C-arm in an angio apparatus in line in one space. A CT-image generating apparatus, an angio-image generating apparatus and a medical image processing system according to the invention are provided by a computer integrally built in the IVR-CT apparatus 10 or a computer connecting to the IVR-CT apparatus 10 online via a communication line. Alternatively, a computer off-line from the IVR-CT apparatus 10 may provide a medical image processing system according to the invention. A case will be described, for example, in which a CT-image generating apparatus, an angio-image generating apparatus and a medical image processing system according to the invention are provided by a computer connecting to the IVR-CT apparatus 10 online via a communication line.

The IVR-CT apparatus 10 mainly includes a bed system 11, an X-ray CT apparatus 12, an radiographic X-ray apparatus (called "angio apparatus" hereinafter) 13, a computer (shown in FIG. 2), an input device 14, and a display device 15. A subject (patient) is mounted on the bed system 11. The X-ray CT apparatus 12 collects X-ray transmission information (projection data) in each direction on the subject. The angio apparatus 13 allows the simultaneous implementation of the operation for inserting a catheter to a subject (that is, operation or examination by a doctor), for example, and radiographic X-ray in parallel. The input device 14 transmits an input signal to the computer. The display device 15 displays an image.

The bed system 11 includes a foot 21 and a table-top 22 on the foot 21. The table-top 22 is configured to allow the mount and movement of the subject thereon in the direction of the body axis (that is, the back and forth direction). The table-top 22 may be configured to allow the movement of the subject in the horizontal and/or vertical directions.

Figure 2:
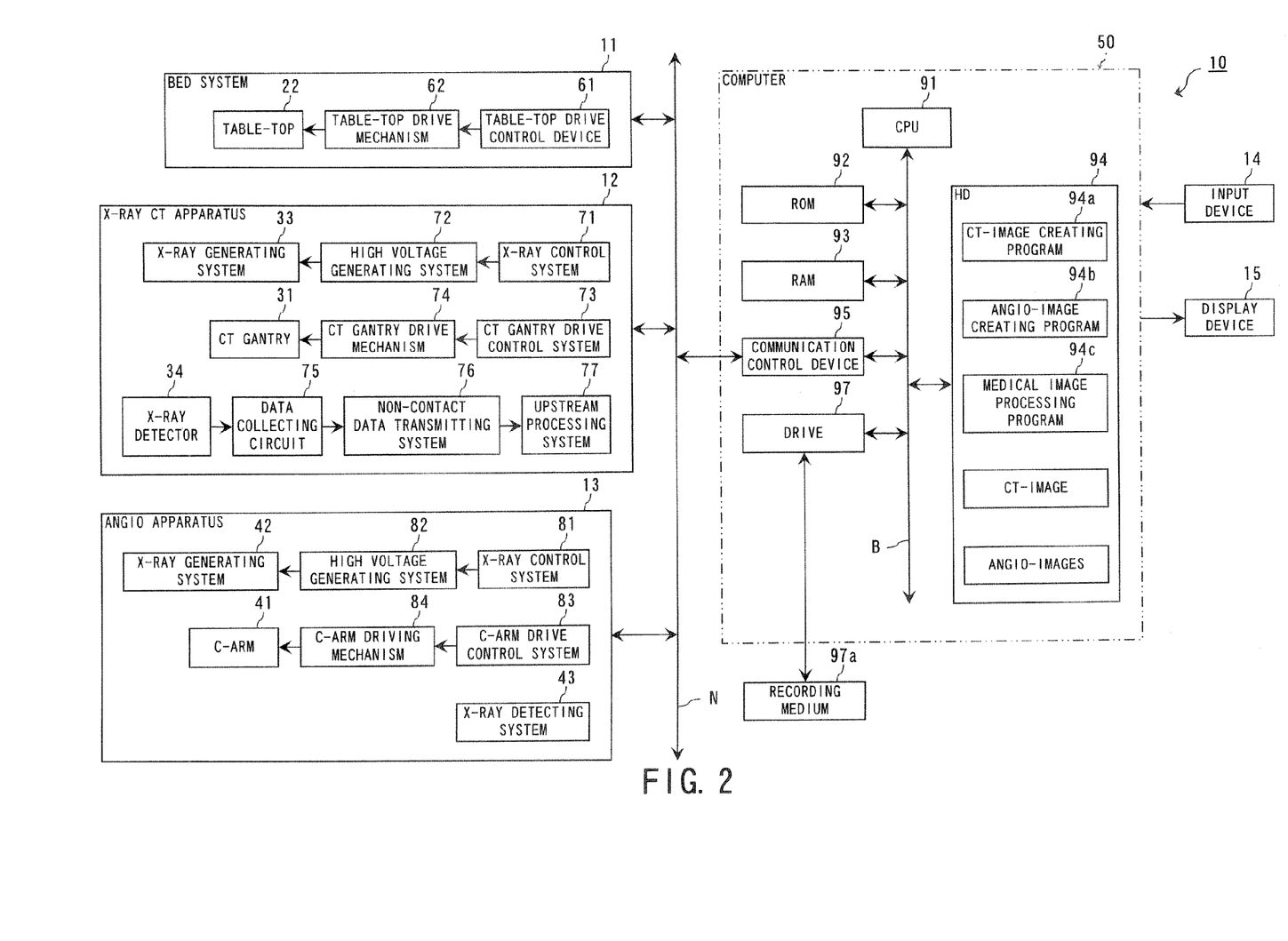
FIG. 2 is a block diagram showing the IVR-CT apparatus and a computer included in the IVR-CT apparatus.

The X-ray CT apparatus 12 includes a CT gantry 31 having a hollow part H to which the table-top 22 can be inserted. An X-ray generating system 33 and an X-ray detector 34 (both of which are shown in FIG. 2) are provided within the CT gantry 31 and around the hollow part H of the X-ray CT apparatus 12 and are rotatable along a given surrounding part. The CT gantry 31 operates in the direction (back and forth direction) which allows the insertion or removal of the table-top 22 to or from the hollow part H there of. Furthermore, the CT gantry 31 can tilt in the back and forth direction in addition to the operation in the back and forth direction with the changeable attitude. Thus, a tomographic X-ray image in a diagonal direction about the subject can be obtained.

The angio apparatus 13 includes a support (called "C-arm" hereinafter) 41 having a substantially C-shape covering the bed system 11 from the side. The C-arm 41 of the angio apparatus 13 includes an X-ray generating system 42 at one end and an X-ray detecting system 43 at the other end, which face against each other. The X-ray detecting system 43 may, for example, have an image intensifier (I.I.) for converting transmitted X-rays through the subject to an optical image, an optical system for correcting the size of the optical image output from the I.I. to a proper size, and an X-ray TV camera for converting the optical image to video signals. The bed system 11 or subject is normally provided between the X-ray generating system 42 and the X-ray detecting system 43. Notably, the term, "normally", typically refers to "during radiographic X-ray" here.

The angio apparatus 13 allows the simultaneous and parallel implementation of the operation or examination by a doctor by inserting a catheter, for example, to the inside of the body of the subject and radiographic X-ray relating to angiography of blood vessels. The C-arm 41 is connected to a fixed arm 44 through a connecting portion 45. The fixed arm 44 externally covers the C-arm 41. The connecting portion 45 allows the C-arm 41 to slide against the fixed arm 44, as indicated by the arrow C. The fixed arm 44 is rotatably mounted to a pivot 47 having one end on the ceiling. The fixed arm 44 and the C-arm 41 rotate about the pivot 47, as indicated by the arrow D. The pivot 47 is mounted onto the ceiling through a base 48. The base 48 moves along a ceiling rail (not shown).

The bed system 11 is fixed according to the invention. The foot 21 is preferably provided out of the way in the operations by the CT gantry 31 and the C-arm 41. Thus, in FIG. 1, the foot 21 in a substantially rectangular parallelepiped form is provided along the edge of the table-top 22. Though the bed system 11 is fixed here, the form is not particularly limited thereto.

The input device 14 is provided near the bed system 11. More specifically, the input device 14 is provided above the foot 21 and by the bed system 11. The input device 14 may include a liquid crystal display (LCD) panel 14a and a numeric keypad 14b, for example. The operations or positioning, for example, of the CT gantry 31 and C-arm 41 may be controlled by operations through the input device 14.

The display device 15 includes a first monitor 15a and a second monitor 15b. The first monitor 15a mainly displays CT-images generated by the computer. The second monitor 15b mainly displays angio-images.

FIG. 2 is a block diagram showing the IVR-CT apparatus 10 and a computer included in the IVR-CT apparatus 10.

As described with reference to FIG. 1, the IVR-CT apparatus 10 includes the bed system 11, the X-ray CT apparatus 12, the angio apparatus 13, the input device 14, the display device 15 and a computer 50. The bed system 11, the X-ray CT apparatus 12, the angio apparatus 13 and the computer 50 are mutually connected over a network N such as a local area network (LAN) functioning as a common signal transmission path.

The bed system 11 has a table-top drive control device 61 and a table-top drive mechanism 62. The table-top drive control device 61 generates a control signal for an operation by the table-top 22 under the control of the computer 50. The table-top drive mechanism drives the table-top 22 by the control signal generated by the table-top drive control device 61.

The X-ray CT apparatus 12 has an X-ray control system 71, a high voltage generating system 72, a CT gantry drive control system 73, and a CT gantry drive mechanism 74. The X-ray control system 71 controls X-rays under the control of the computer 50. The high voltage generating system 72 applies high voltage generated serially or periodically to the X-ray generating device 33 through a slip ring (not shown). The CT gantry drive control system 73 generates a control signal for an operation by the CT gantry 31 under the control of the computer 50. The CT gantry drive mechanism 74 drives the CT gantry 31 by the control signal generated by the CT gantry drive control system 73. The X-ray CT apparatus 12 has a data collecting circuit 75, a non-contact data transmitting system 76 and an upstream processing system 77.

The data collecting circuit 75 includes, for each channel, an I-V converter (not shown), an integrator (not shown), a preamplifier (not shown) and an A-D converter (not shown). The I-V converter converts a current signal of each channel of the X-ray detector 34 to voltage. The integrator integrates voltage signals in synchronization with the period of the exposure to X-rays and periodically. The preamplifier amplifies an output signal of the integrator. The A-D converter converts an output signal of the preamplifier to a digital signal.

The non-contact data transmitting system 76 optically or magnetically implements the non-contact data transmission of a digital signal (pure data), which is an output of the data collecting circuit 75.

The upstream processing system 77 performs upstream processing on the pure data received through the non-contact data transmitting system 76 including correcting the unevenness in sensitivity among channels and correcting an extreme decrease in signal strength or signal drop off due to an X-ray strong absorber typically such as a metallic part and generates projection data.

The angio apparatus 13 has an X-ray control system 81, a high voltage generating system 82, a C-arm drive control system 83, and a C-arm driving mechanism 84. The X-ray control system 81 controls X-rays under the control of the computer 50. The high voltage generating system 82 applies high voltage generated serially or periodically to the X-ray generating device 42. The C-arm drive control system 83 generates a control signal for an operation by the C-arm 41 under the control of the computer 50. The C-arm driving mechanism 84 drives the C-arm 41 by the control signal generated by the C-arm drive control system 83.

The computer 50 has basic hardware including a central processing unit (CPU) 91, a read only memory (ROM) 92, a random access memory (RAM) 93 and a hard disk (HD) 94. The CPU 91 is mutually connected to the hardware components of the computer 50 via a bus B functioning as a common signal transmission path. The computer 50 may have a communication control device 95 and a drive 97.

In response to the input of a command resulting from an operation on the input device 14 by a user, for example, the CPU 91 executes a program stored in the ROM 92. The CPU 91 loads to the RAM 93 and executes a program stored in the HD 94, a program transferred from the network N, received by the communication control device 95 and installed in the HD 94 or a program invoked from a removable recording medium 97a and installed in the HD 94. The recording medium 97a may be a flexible disk, a compact disc-read only memory (CD-ROM), a magneto optical (MO) disk, a digital versatile disc (DVD), magnetic disk or semiconductor memory installed in the drive 97. As a result of the execution of a program, the computer 50 functions as the CT-image generating apparatus, the angio-image generating apparatus and the medical image processing system.

The ROM 92 is a non-volatile storage device that stores an initial program loading (IPL) for reading an operating system (OS) from the HD 94 and expanding and starting the OS in the RAM 93, a basic input/output system (BIOS) for controlling peripheral apparatus such as the input device 14 and the drive 97 and data.

The RAM 93 is a volatile storage device to be used as a work memory of the CPU 91 and for temporary storage. The ROM 92 may be a mask ROM, which is not overwritable, or a programmable ROM (PROM), which is overwritable.

The HD 94 is a storage device that stores programs (including a CT-image generating program 94a functioning as an application program, an angio-image generating program 94b, a medical image processing program 94c and the OS) installed in a medical image processing system 60 and data (including three-dimensional CT-images and angio-images) required for processing by the CPU 91. The OS can provide the application of a graphical user interface (GUI), which allows a basic operation to be performed by the input device 14 by using a graphic on the screen of the display device 14.

The communication control device 95 is a communication interface (I/F) including an institute of electrical and electronics engineers (IEEE) 1394 port, a universal serial bus (USB) port, and a network interface card (NIC) for the LAN connection and performs communication control under a standard. The communication control device 95 has a function allowing the connection to the network N, which is the Internet, through a telephone line by an analog modem or a terminal adapter (TA), a digital service unit (DSU) or an asymmetric digital subscriber line (ADSL) modem, for example. Thus, the computer 50 can connect to the network N from the communication control device 95.

The recording medium 97a is removable from the drive 97, and the drive 97 reads out and outputs data (including a program) recorded on the recording medium 97a to the bus B and writes the data supplied via the bus B to the recording medium 97a. Here, the program to be executed by the CPU 91 can be temporarily or permanently stored (recorded) in the recording medium 97a. The recording medium 97a can be provided as so-called "package software".

In the computer 50 having this construction, the CPU 91 executes the CT-image generating program 94a so that the bed system 11 and the X-ray CT apparatus 12 can be controlled to generate and store the three-dimensional CT-images. Furthermore in the computer 50, the CPU 91 executes the angio-image generating program 94b to generate and store the angio-images. The CPU 91 executes the medical image processing program 94c to generate and display a projected image in the direction of imaging of a required angio-image as the direction of the projection.

Figure 3:
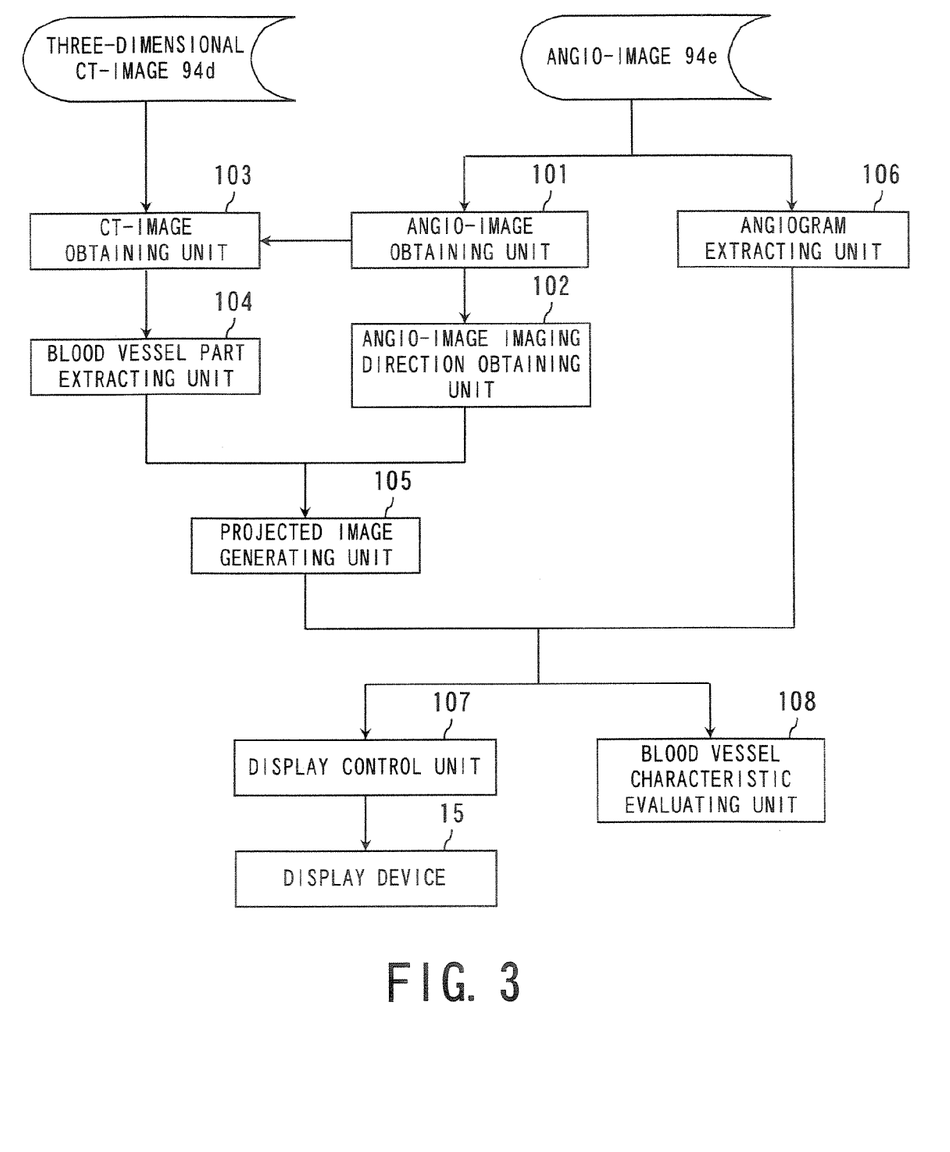
FIG. 3 is a functional block diagram showing a first embodiment of a medical image processing system.

FIG. 3 is a functional block diagram showing a first embodiment of a medical image processing system functioning by the execution of the medical image processing program 94c.

The CPU 91 executes the medical image processing program 94c installed in the computer so that the computer 50 can function as an angio-image obtaining unit 101, an angio-image imaging direction obtaining unit 102, a CT-image obtaining unit 103, a blood vessel part extracting unit 104, a projected image generating unit 105, an angiogram extracting unit 106, a display control unit 107 and a blood vessel characteristic evaluating unit 108. The computer 50 may function as a direction-of-vision correspondence information generating unit (not shown). The CPU 91 executes the medical image processing program 94c installed in the computer 50 so that the computer 50 can function as a medical image processing system.

The angio-image obtaining unit 101 has a function to obtain a required angio-image 94e selected by an operation on the input device 14 by a user from multiple chronological angio-images stored by a storage device such as the HD 94.

The angio-image imaging direction obtaining unit 102 has a function to obtain the direction of imaging of the angio-image (direction of vision of an observer) as incidental information included in the data of the angio-image 94e.

The CT-image obtaining unit 103 has a function to obtain a required three-dimensional CT-image 94d corresponding to the angio-image 94e obtained by the angio-image obtaining unit 101 from the three-dimensional CT-image stored by a storage device such as the HD 94. For example, the CT-image obtaining unit 103 obtains the three-dimensional CT-image 94d having the closest heartbeat phase to that of the angio-image 94e.

The blood vessel part extracting unit 104 has a function to extract a blood vessel part (blood vessel ramifications) contained in the three-dimensional CT-image 94d based on an input signal input to the computer 50 as a result of an operation for locating a blood vessel part contained in the three-dimensional CT-image 94d by a user through the input device 14. Alternatively, the blood vessel part extracting unit 104 may have a function to extract a blood vessel part contained in the three-dimensional CT-image 94d automatically from a difference in intensity, for example, based on the three-dimensional CT-image 94d.

The projection image generating unit 105 has a function to generate a three-dimensional CT curved-planer projected image, as a three-dimensional projected image, by projecting the blood vessel part extracted by the blood vessel part extracting unit 104 in a predetermined direction such as the direction of imaging of the angio-image 94e obtained by the angio-image imaging direction obtaining unit 102. And the projection image generating unit 105 has a function to generate for generating a three-dimensional CT curved-planer projected image corresponding to a direction of a projection after a manual operation operates the direction of the projection.

The angiogram extracting unit 106 has a function to extract an angiogram (blood vessel part) contained in the angio-image 94e based on an input signal input to the computer 50 as a result of an operation for locating the angiogram contained in the angio-image 94e by a user through the input device 14. Alternatively, the angiogram extracting unit 106 may have a function to extract an angiogram contained in the angio-image 94e automatically from a difference in intensity, for example, based on the angio-image 94e. If the angio-image is a difference image, the angiogram extracting unit 106 may be omitted.

The display control unit 107 has a function to make display the three-dimensional CT curbed-planer projected image generated by the projected image generating unit 105 and the angiogram extracted by the angiogram extracting unit 106 on the display device 15 one over another.

The projected image generating unit 105 has a function to generate a three-dimensional CT curbed-planar projected image by projecting in the direction of the projection after a changing operation based on an input signal input to the computer 50 as a result of a manual operation in the direction of the projection by a user through the input device 14.

The blood vessel characteristic evaluating unit 108 has a function to evaluate a characteristic of a blood vessel, such as the evaluation of the rate of a narrowing, based on the three-dimensional CT curved-planar projected image generated by the projected image generating unit 105.

The direction-of-vision correspondence information generating unit has a function to generated direction-of-vision correspondence information including a correspondence established between mutual directions of visions of the direction of the projection of the three-dimensional CT curbed-planar projected image displayed on the display device 15 and the direction of imaging of the angio-image 94e.

Though, according to the invention, the single computer 50 functions as the CT-image generating apparatus, the angio-image generating apparatus and the medical image processing system, the invention is not limited to this case. The computer 50 may be configured to function as the CT-image generating apparatus and the angio-image generating apparatus, and another computer such as a viewer and a work station mutually connecting to the network N may be configured to function as the medical image processing system. Alternatively, the computer 50 may be configured to function as the CT-image generating apparatus and the angio-image generating apparatus, and a computer offline from the network N may be configured to function as the medical image processing system.

Next, an operation for generating the CT-images and the angio-images by the IVR-CT apparatus 10 will be described with reference to FIGS. 1 and 2.

First of all, a user operates the input device 14 to input a signal of a command to execute the CT-image generating program 94a from the input device 14 to the CPU 91 of the computer 53. When the signal of the execution command is input to the CPU 91, the CPU 91 controls the table-top drive control device 61 of the bed system 11 and the X-ray control system 71 and the CT gantry drive control system 73 of the X-ray CT apparatus 12 to perform radiographic X-ray on the subject mounted on the table-top 22 of the bed system 11. Under the control of the computer 50, the high voltage serially or periodically generated by the high voltage generating system 72 is applied to the X-ray generating system 33 through the slip ring (not shown). Thus, the X-rays are irradiated from the X-ray generating system 33 toward the subject, and the X-ray detector 34 detects the X-rays transmitted through the subject.

In the I-V converter (not shown) of the data collecting circuit 75, current signals of the channels of the X-ray detector 34 are converted to voltage, and the integrator (not shown) integrates the voltage signals periodically and in synchronization with the period of irradiation of X-rays. The preamplifier (not shown) of the data collecting circuit 75 amplifies the output signal of the integrator, and the A-D converter (not shown) converts the output signal of the preamplifier to a digital signal.

Figure 4:
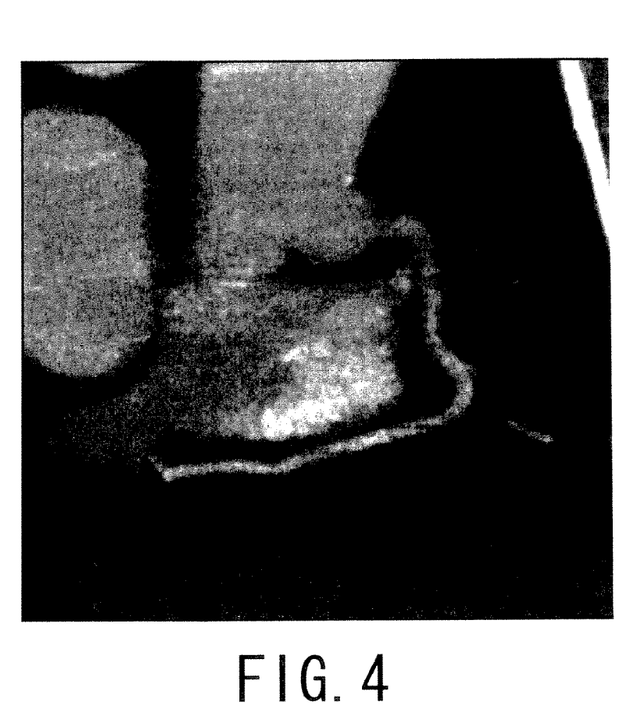
FIG. 4 is a diagram showing an example of a three-dimensional CT-image including a blood vessel part.

The non-contact data transmitting system 76 implements the non-contact, optical or magnetic data transmission of pure data, which is the output of the data collecting circuit 75. Next, the upstream processing system 77 performs upstream processing on the pure data received through the non-contact data transmitting system 76 including correcting the unevenness in sensitivity among channels and correcting an extreme decrease in signal strength or signal drop off due to an X-ray strong absorber typically such as a metallic part and generates projection data. The projection data generated by the upstream processing system 77 is projection data round, that is, at "360°" or "180°+the view angle about the subject". The projection data is stored as digital data in the HD 94 of the computer 50.

when the CPU 91 performs image reconstruction processing based on the projection data, the three-dimensional CT-image including the blood vessel part is generated. The three-dimensional CT-image is displayed on the first monitor 15a of the display device 15 and also is stored in the HD 94 of the computer 50. FIG. 4 is a diagram showing an example of the three-dimensional CT-image including a blood vessel part to be displayed on the first monitor 15a. Notably, the three-dimensional CT-image may be stored in a memory, the HD 94 or the recording medium 97a through the drive 97.

Figure 5:
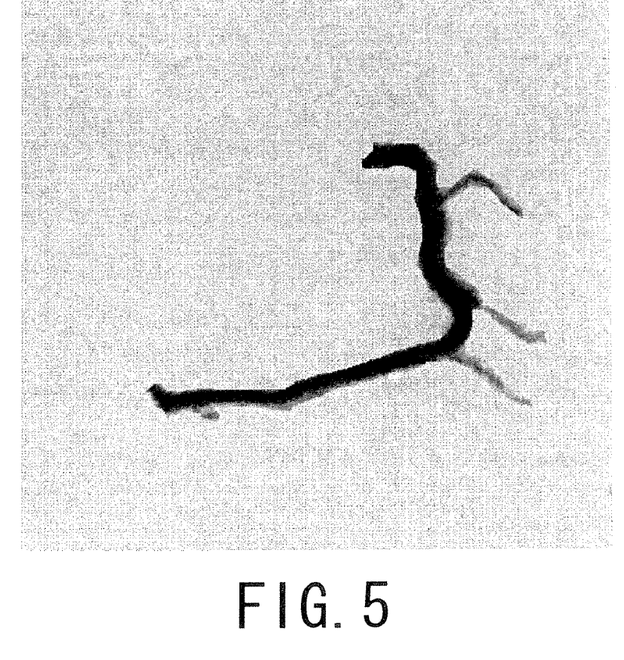
FIG. 5 is a diagram showing an example of an angio-image 94e including a coronary angiogram.

On the other hand, a user operates the input device 14 to input a signal of the command to execute the angio-image generating program 94b from the input device 14 to the CPU 91 of the computer 50. When the signal of the execution command to the CPU 91, the angio apparatus 13 is controlled to generate the angio-image by coronary angiography. The angio-image is displayed on the second monitor 15b of the display device 15 and is stored as digital data in the HD 94 of the computer 50. FIG. 5 is a diagram showing an example of the angio-image including a coronary angiogram to be displayed on the second monitor 15b. Notably, the angio-image may be stored in a memory, the HD 94 or the recording medium 97a through the drive 97.

Here, the generation of the angio-image may have two modes, for example. That is, "digital angiography (DA) mode" and "digital subtraction angiography (DSA) mode" may be implemented. In "DA mode", normal radiographic X-ray is performed by the angio apparatus 13 to simply generate an X-ray image including (the flow of) a contract medium and display/store the X-ray image. In "DSA mode", the difference image between an X-ray image (mask image) excluding (the image of) a contract medium and an X-ray image (contrast image or live image) including (the image of) a contract medium is captured (which is subtraction processing) so that the X-ray image having the contract medium or the flow more clearly can be displayed/stored.

Next, a medical image processing method according to this embodiment will be described with reference to the flowchart shown in FIG. 6.

A user operates the input device 14 to input the signal of a command to execute the medical image processing program 94c from the input device 14 to the CPU 91 of the computer 50.

The signal of the execution command is input to the CPU 91, and the user operates the input device 14 to obtain the required angio-image 94e selected from multiple chronological angio-images stored by a storage device such as the HD 94 (step S1). Next, the direction of imaging of the angio-image 94e (the direction of vision of an observer) is obtained as incidental information included in the data of the angio-image 94e obtained by step S1 (step S2).

Furthermore, the required three-dimensional CT-image 94d corresponding to the angio-image 94e obtained by step S1 is obtained from the three-dimensional CT-images stored by a storage device such as the HD 94 (step S3). In step S3, the three-dimensional CT-image 94d having the closest heartbeat phase to that of the angio-image 94e is obtained based on the information on the heartbeat phase, for example.

Next, the user performs an operation for locating a blood vessel part contained in the three-dimensional CT-image 94d by using the input device 14. The blood vessel part is extracted from the three-dimensional CT-image 94d showing the information within a three-dimensional area relating to a desired subject based on the input signal input to the computer 50 by the locating operation. Alternatively, a blood vessel part contained in the three-dimensional CT-image 94d is extracted from a difference in a CT value or intensity, for example, in the three-dimensional CT-image 94d (step S4).

An area of the blood vessel part is obtained by steps of [1] selecting, on the three-dimensional CT-image 94d, a part of the blood vessel selected by the user, [2] extracting the area having a contract medium (that is, the area having blood) by performing threshold processing on CT values or intensities, for example, in the three-dimensional image data, and [3] extracting the area continuing to the point selected by the user from the extracted area of the contract medium (area of blood). Thus, blood vessel information indicating the state of blood vessel ramifications can be obtained.

In an alternative method for extracting the area of a blood vessel part, the lining membranes of the blood vessels may be obtained by steps of [1] selecting, by a user, a part of selected blood vessels on the three-dimensional CT-image 94d, [2] extracting the area having a contract medium (area having blood) by performing threshold processing on CT values or intensities, for example, in the three-dimensional image data, and [3] obtaining the lining membranes continuing to the point part selected by the user from the extracted area of the contract medium (area of blood). Thus, the blood vessel information indicating the state of the blood vessel ramifications may be obtained from the lining membranes (as disclosed in the specification of Japanese Unexamined Patent Application Publication No. 2005-63902). The range of the lining membranes may be selected manually by a user.

Next, the three-dimensional CT curved-planer projected image is generated as a result of the projection of the blood vessel part extracted by step S4 in the direction of imaging of the angio-image obtained by step S2 (step S5).

An operation for locating the angiogram contained in the angio-image 94e is performed by a user by using the input device 14. Based on the input signal input to the computer 50 by the locating operation, the angiogram contained in the angio-image 94e relating to a desired subject is extracted. Alternatively, the angiogram contained in the angio-image 94e may be automatically extracted from a difference in intensity, for example, in the angio-image 94e (step S6). If the angio-image 94e is a difference image, step S6 may be omitted.

Next, the three-dimensional CT curved-planer projected image generated by step 5S and the angiogram extracted by step S6 are made to display on the display device 15 one over another (step S7). FIG. 7 is a diagram showing an example of the superimposition display of the three-dimensional CT curved-planer projected image and the angiogram. The CT curved-planer projected image improves the visibility for registration by displaying the coronary part in a predetermined area excluding the image of the ventricle part, for example.

Here, the user uses the input device 14 to determine whether an operation is performed for changing the direction of the projection of the three-dimensional CT curved planer projected image or not (step S8). If "Yes" as a result of the determination in step S8, that is, if it is determined that the user has used the input device 14 to perform an operation for changing the direction of the projection of a three-dimensional curved-planer projected image, the three-dimensional CT curved-planer projected image is generated in the changed direction of the projection based on the input signal input to the computer 50 (step S5). The user uses the input device 14 to rotate the three dimensional CT curved-planer projected image (volume) on the display screen such that the three-dimensional CT curved-planer projected image in the changed direction of the projection can be displayed over the angiogram.

Figure 8:
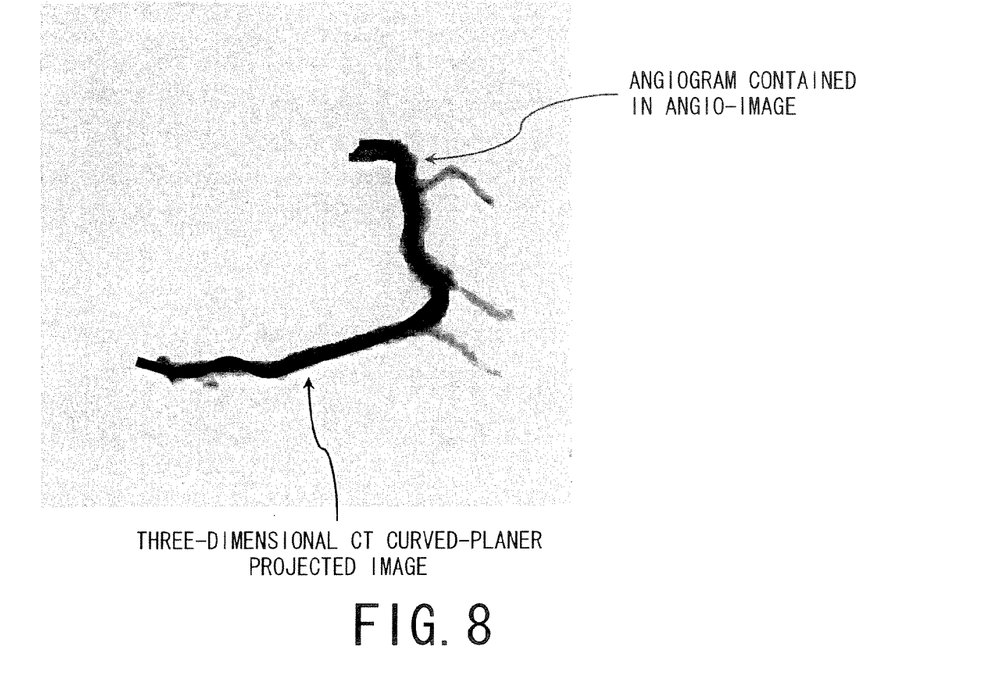
FIG. 8 is a diagram showing an example of the superimposition display of the three-dimensional CT curved-planer projected image in the changed direction of the projection and the angiogram.

FIG. 8 is a diagram showing an example of the superimposition display of the three-dimensional CT curved-planer projected image in the changed direction of the projection and the angiogram. On the other hand, if "No" as a result of the determination in step S8, that is, if it is determined that the user has not performed the operation for changing the direction of the projection by using the input device 14, direction-of-vision correspondence information is generated including a correspondence of the mutual directions of points of vision of the direction of the projection of the three-dimensional CT-curved planer projected image and the direction of imaging of the angio-image, which are superimposed. In addition, a characteristic, such as the rate of a narrowing, of the blood vessel is evaluated on the CT curved-planer projected image superimposed by step S7 (step S9). The generated direction-of-vision correspondence information is stored in a storage device such as the HD 94.

Step S8 is not always required, but a characteristic of the blood vessel may be always evaluated on the CT curved-planer projected image in the direction of the projection obtained by step S2. Alternatively, in step S8 may be performed by a user by instructing not to perform the operation for changing the direction of the projection by clicking a position confirmation button (not shown) on the screen.

Next, in order to perform percutaneous coronary intervention (PCI) for extending the coronary artery narrowed by arteriosclerosis by using a catheter, the three-dimensional CT curved-planer projected image is displayed on the first monitor 15a of the display device 15. The direction of the projection of the three-dimensional CT curved-planer projected image is confirmed by changing the angle of projection of the CT curved-planer projected image arbitrarily and then clicking a confirmation button (not shown) on the screen by a user by using the input device 14. Here, the three-dimensional CT curved-planer projected image may be displayed on the screen by obtaining left anterior oblique view/right anterior oblique view (LAO/RAO) or Cranial view/Caudal view (CRA/CAU), which is the angle information of the C-arm 14

(equivalent to the direction of radiographic X-ray), by using the direction-of-vision correspondence information when the direction of the projection of the three-dimensional CT curved-planer projected image is changed.

When the direction of the projection of the three-dimensional C T curved-planer projected image is confirmed, a position of the C-arm 41 may be controlled so as to obtain the angio-image of the direction of imaging of the angio-image corresponding to (or substantial equal to) the direction of the projection by using the direction of the projection of the three-dimensional CT curved-planer projected image displayed on the first monitor 15$a$ and the direction-of-vision correspondence information.

According to the medical image processing system and the medical image processing method of this embodiment, the direction of the projection of the CT curved-planer projected image is preset based on the direction of imaging of the angio-image 94$e$, and the CT curved-planer projected image and the angiogram are registered manually. Thus, the direction of the projection, which is the same as the direction of imaging of the angio-image 94$e$ can be reproduced on the three-dimensional CT-image 94$d$. Furthermore, the information on the direction of radiographic X-ray by the angio apparatus 13 can be obtained from the direction of the projection of the three-dimensional CT-image 94$d$ by obtaining the information that establishes the correspondence of the directions of imaging of the angio-image 94$e$ and the three-dimensional CT-image 94$d$.

According to the medical image processing system and medical image processing method of this embodiment, a CT curved-planer projected image is displayed in the direction of the projection, which is the same as the direction of imaging of the angio-image 94$e$, so that the evaluation on a characteristic of the blood vessels such as evaluation on the rate of a narrowing can be performed more accurately.

Furthermore, according to the medical image processing system and medical image processing method of this embodiment, the angio-image 94$e$ in the direction of vision corresponding to the direction of the projection of the displayed three-dimensional curved-planer projected image can be obtained, which can perform PCI in a shorter operation time and with the smaller amount of irradiation to a subject.

Figure 9:
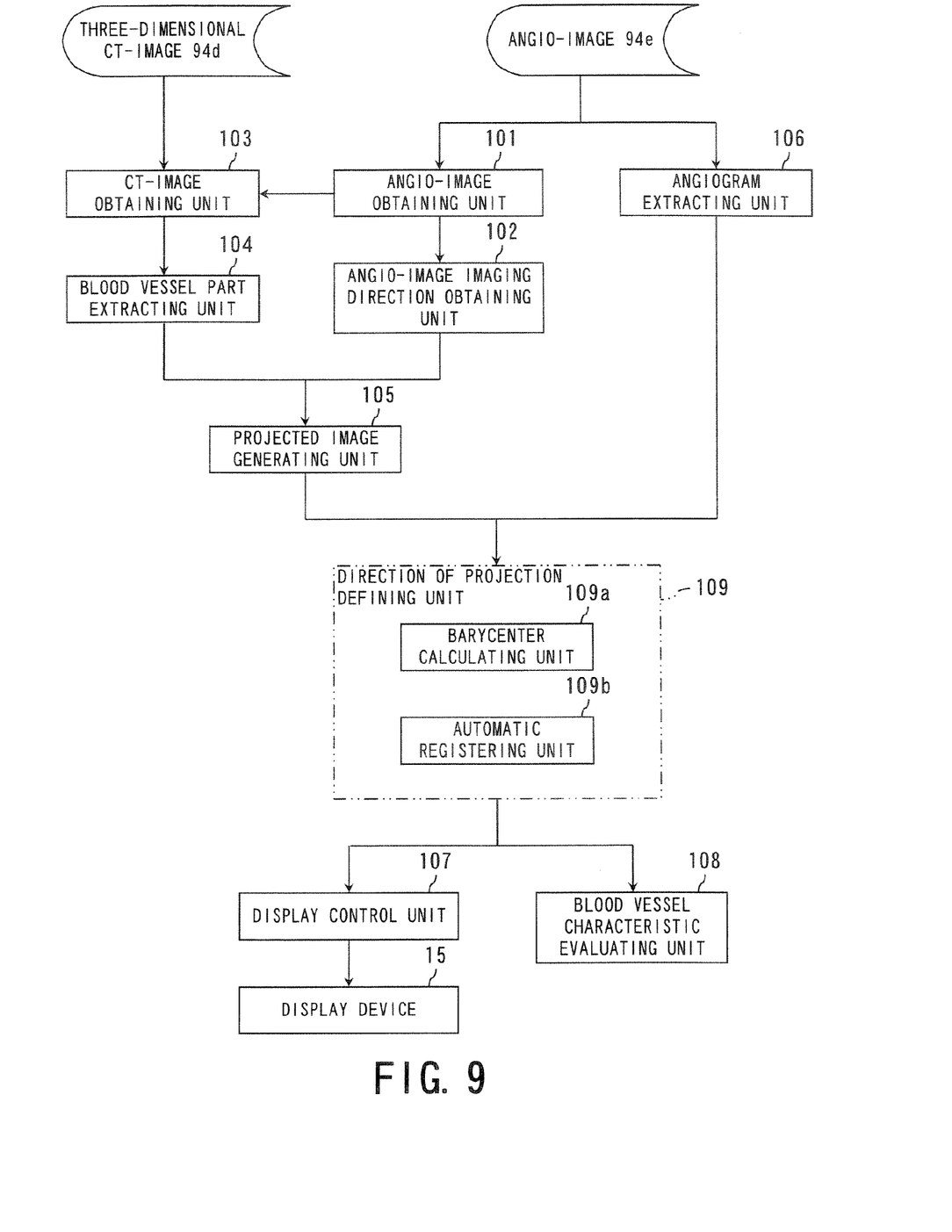
FIG. 9 is a functional block diagram showing a second embodiment of a medical image processing system functioning as a result of the execution of the medical image processing program.

FIG. 9 is a functional block diagram showing a second embodiment of a medical image processing system functioning as a result of the execution of the medical image processing program 94$c$.

The CPU 91 executes the medical image processing program 94$c$ installed in the computer so that the computer 50 can function as an angio-image obtaining unit 101, an angio-image imaging direction obtaining unit 102, a CT-image obtaining unit 103, a blood vessel part extracting unit 104, a projected image generating unit 105, a angiogram extracting unit 106, a direction of projection defining unit 109, a display control unit 107 and a blood vessel characteristic evaluating unit 108.

The direction of projection defining unit 109 has a function to get a direction of the projection of the three-dimensional CT curved-planer projected image corresponding (resembling) to the direction of imaging of the angio-Image 94$e$, by comparing the blood vessel part contained in the three-dimensional CT curved-planer projected image and the angiogram contained in the angio-image. Specifically, the direction of projection defining unit 109 has a barycenter calculating unit 109$a$ and an automatic registering unit 109$b$.

The barycenter calculating unit 109$a$ has a function to calculate a barycenter of the three-dimensional CT curved-planer projected image generated by the projected image generating unit 105 and a barycenter of the angiogram extracted by the angiogram extracting unit 106. The barycenter calculating unit 109$a$, for example, sets three points on the blood vessel part contained in the three-dimensional CT curved-planer projected image and three points on the angiogram. Then, the barycenter calculating unit 109$a$ calculates the barycenter of the three-dimensional CT curved-planer projected image by three points on the blood vessel part contained in the three-dimensional CT curved-planer projected image, and the barycenter of the angiogram by three points on the angiogram.

The automatic registering unit 109$b$ semi-automatically has a function to rotate and register (change the direction of the projection) the three-dimensional CT curved-planer projected image such that the vectors of positions on the lining membranes of the blood vessels part contained in the three-dimensional CT-image 94$d$ can be placed most closely over the vector of positions on the lining membranes of the angiogram extracted by the angiogram extracting unit 106. The automatic registering unit 109$b$ has a function to semi-automatically rotate and register (change the direction of the projection) the three-dimensional CT curved-planer projected image such that the barycenter of the three-dimensional CT curved-planer projected image and the barycenter of the angiogram, which are calculated by the barycenter calculating unit 109$a$, can be registered.

In FIG. 9, the same reference numerals are given to the same components as those shown in FIG. 3, and the description will be omitted herein.

Figure 10:
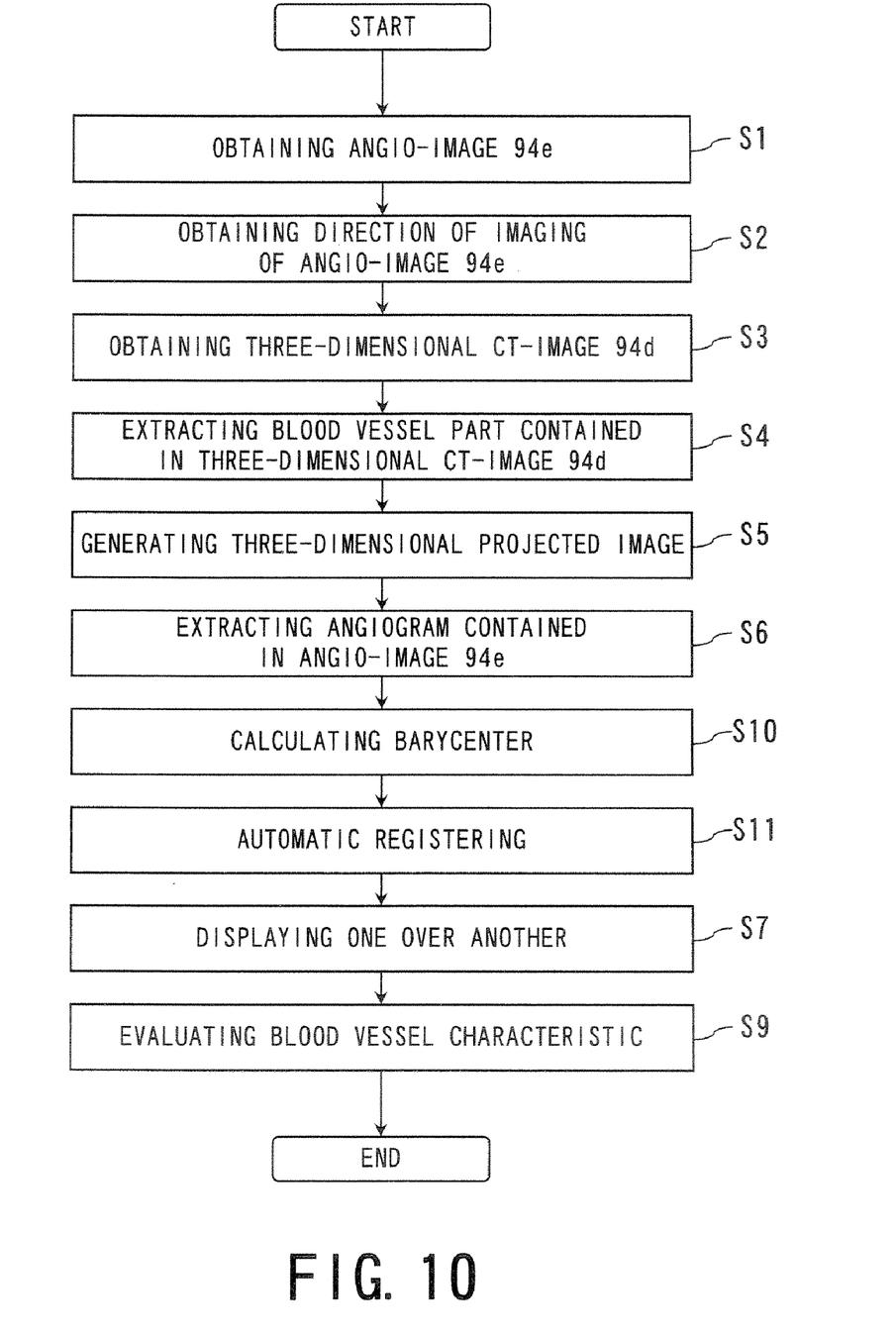
FIG. 10 is a medical image processing method according to this embodiment will be described with reference to the flowchart.

Next, the medical image processing method according to this embodiment will be described with reference to the flowchart shown in FIG. 10. In the flowchart shown in FIG. 10, the same reference numerals are given to the same steps as the steps of the flowchart shown in FIG. 6, and the description will be omitted herein.

After the angiogram is extracted by step S6, the barycenter of the three-dimensional CT curved-planer projected image generated by step S5 and the barycenter of the angiogram extracted by step S6 are calculated (step S10).

The three-dimensional CT curved-planer projected image semi-automatically rotates and registers such that the vectors of positions on the lining membranes of the blood vessels part contained in the three-dimensional CT-image 94$d$ generated by step S5 can be placed most closely over the vector of positions on the lining membranes of the angiogram extracted by step S6 (step S11). In step S11, the three-dimensional CT curved-planer projected image semi-automatically rotates and registers such that the barycenter of the three-dimensional CT curved planer projected image and the barycenter of the angiogram, which are calculated by step S10, can be registered.

Next, the three-dimensional CT curved-planer projected image rotated and registered by step S11 and the angiogram extracted by step S6 are made to display one over another by the display device 15 (step S7).

Figure 6:
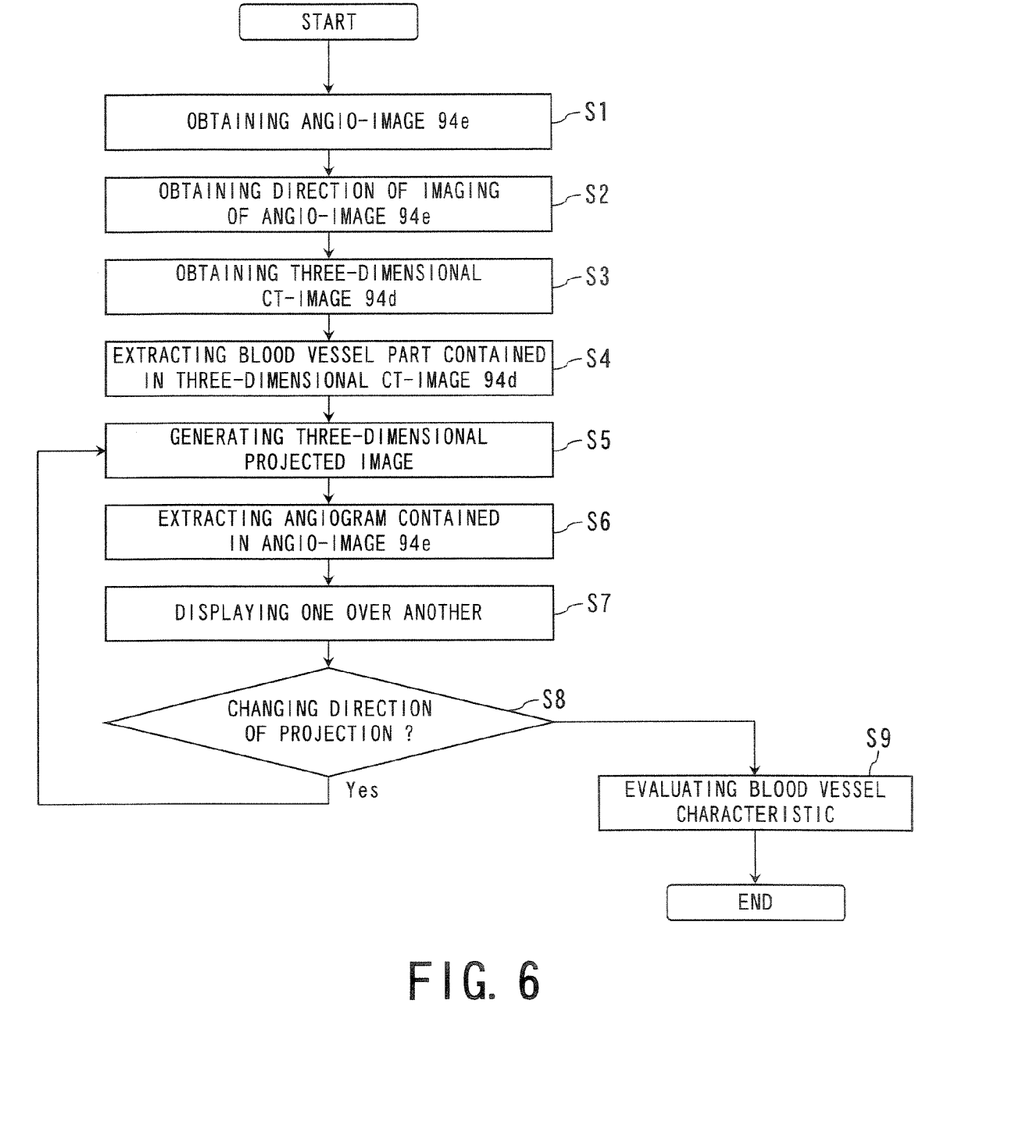
FIG. 6 is a medical image processing method according to this embodiment will be described with reference to the flowchart.
Figure 7:
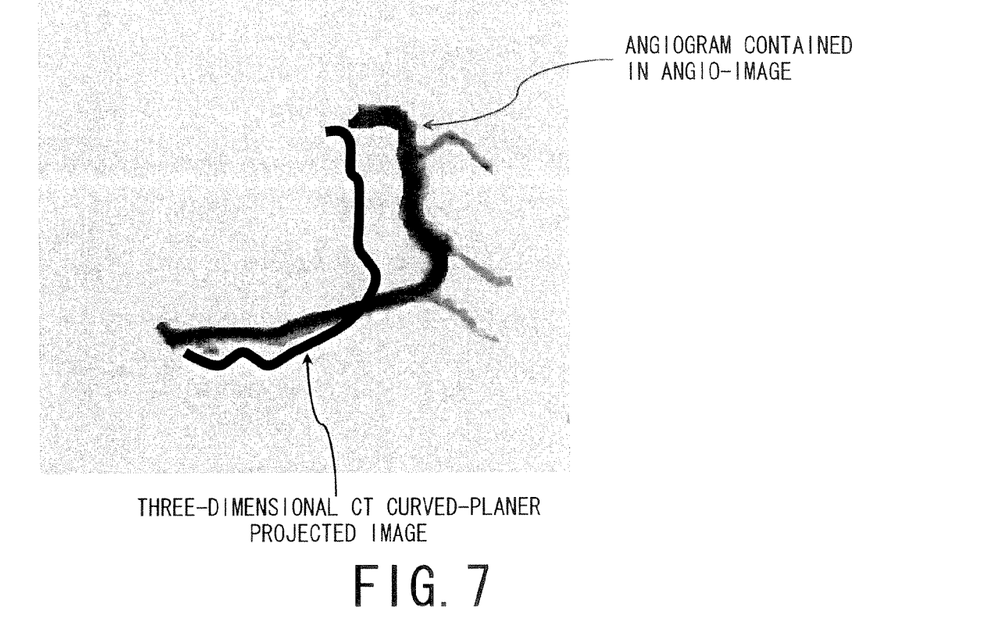
FIG. 7 is a diagram showing an example of the superimposition display of the three-dimensional CT curved-planer projected image and the angiogram.

The first embodiment of the medical image processing system may include the barycenter calculating unit 109$a$ and the automatic positioning unit 109$b$, and steps S10 and S11 may be performed after step S6 in the flowchart shown in FIG. 6 so that the registration of the three-dimensional CT curved-planer projected image and the angiogram can be manually and semi-automatically performed.

According to this embodiment, the three-dimensional CT-images and the angio-images are stored in the HD 94 of the computer 50 by using the IVR-CT apparatus 10. However, the invention is not limited thereto. The three-dimensional CT-images and the angio-images collected by the remote X-ray CT apparatus 12 and the angio apparatus 13 may be transmitted to the computer 50 through communication lines, and the three-dimensional CT-images and the angio-images may be stored in the HD 94 of the computer 50.

Having described the case that a CT curved-planer projected image is obtained according to this embodiment of the invention, the invention is not limited to the case. The three-dimensional projected image of a CT-image may be obtained by other projecting methods.

According to the medical image processing system and the medical image processing method of this embodiment, the direction of the projection of a CT curved-planer projected image is preset based on the direction of imaging of the angio-image 94e, and the CT curved-planer projected image and the angiogram are registered semi-automatically. Thus, the same direction of the projection as the direction of imaging of the angio-image 94e can be reproduced on the three-dimensional CT-image 94d. The information on the direction of imaging by the angio apparatus 13 can be obtained from the direction of the projection of the three-dimensional CT-image 94d by obtaining correspondence information between the angio-image 94e and the three-dimensional CT-image 94d.

Still further, according to the medical image processing system and the medical image processing method of this embodiment, a CT curved-planer projected image can be displayed in the same direction of the projection as the direction of imaging of the angio-image 94e. Thus, the evaluation of a characteristic of blood vessels, such as the evaluation of the rate of a narrowing, can be evaluated more accurately by displaying a CT curved-planer projected image in the same direction of the projection as the direction of imaging of the angio-image 94e.

In addition, according to the medical image processing system and the medical image processing method of this embodiment, the angio-image 94e in the direction of vision equivalent to the direction of the projection of the displayed three-dimensional CT curved-planer projected image can be obtained. Thus, PCI can be performed in a shorter operation time and with a smaller amount of exposure to a subject.

What is claimed is:

1. A medical image processing system comprising:
   an angio-image obtaining unit for obtaining a required angio-image from multiple chronological angio-images;
   an angio-image imaging direction obtaining unit for obtaining a direction of imaging as incidental information included in data on the required angio-image;
   a CT-image obtaining unit for obtaining a three-dimensional CT-image corresponding to the required angio-image;
   a blood vessel part extracting unit for extracting a blood vessel part in the three-dimensional CT-image;
   a projected image generating unit for generating a three-dimensional projected image by projecting the blood vessel part, and for generating a three-dimensional projected image corresponding to a direction of a projection after a manual operation operates the direction of the projection; and
   a display control unit for making display the three-dimensional projected image and the angio-image.

2. A medical image processing system according to claim 1, wherein the three-dimensional projected image is considered to be a three-dimensional CT curved-planar projected image.

3. A medical image processing system according to claim 1, further comprising a direction-of-vision correspondence information generating unit for generating a direction-of-vision correspondence information including a correspondence established between the direction of the projection after it was changed based on the manual operation and the direction of imaging, wherein a position of a C-arm on an angio apparatus be controlled so as to obtain the direction of imaging corresponding to the direction of the projection after it was changed based on the manual operation and the direction-of-vision correspondence information.

4. A medical image processing system according to claim 1, further comprising an angiogram extracting unit for extracting an angiogram contained in the required angio-image, wherein the display control unit makes display the three-dimensional projected image corresponding to the direction of the projection after it was changed based on the manual operation and the angiogram one over another.

5. A medical image processing system according to claim 1, further comprising a blood vessel characteristic evaluating unit for evaluating a characteristic of a blood vessel, based on the three-dimensional projected image corresponding to the direction of the projection after it was changed based on the manual operation.

6. A medical image processing system according to claim 1, wherein the CT-image obtaining unit obtains the three-dimensional CT-image that a heartbeat phase is the nearest to the required angio-image of indispensability.

7. A medical image processing system comprising:
   an angio-image obtaining unit for obtaining a required angio-image from multiple chronological angio-images;
   an angio-image imaging direction obtaining unit for obtaining a direction of imaging as incidental information included in data on the required angio-image;
   a CT-image obtaining unit for obtaining a three-dimensional CT-image corresponding to the required angio-image;
   a blood vessel part extracting unit for extracting a blood vessel part in the three-dimensional CT-image;
   a direction of projection defining unit for defining a direction of a projection;
   a projected image generating unit for generating a three-dimensional projected image by projecting the blood vessel part in the direction of the projection;
   an angiogram extracting unit for extracting an angiogram contained in the required angio-image; and
   a display control unit for making display the three-dimensional projected image and the angiogram,
   wherein the direction of projection defining unit defines the direction of the projection of the three-dimensional projected image corresponding to the direction of imaging of the required angio-image, by comparing the blood vessel part and the angiogram.

8. A medical image processing system according to claim 7, wherein the three-dimensional projected image is considered to be a three-dimensional CT curved-planar projected image.

9. A medical image processing system according to claim 7, wherein the projected image generating unit generates a three-dimensional projected image corresponding to a direction of a projection after it was changed based on a manual operation, and the display control unit makes display the three-dimensional projected image corresponding to the direction of the projection after it was changed based on the manual operation and the angiogram one over another.

10. A medical image processing system according to claim 7, wherein the direction of projection defining unit has a barycenter calculating unit for calculating a barycenter of the three-dimensional projected image and a barycenter of the angiogram, and an automatic registering unit for rotating and registering the three-dimensional projected image such that the barycenter of the three-dimensional projected image and the barycenter of the angiogram can be registered, wherein the projected image generating unit generates the three-dimensional projected image corresponding to the direction of the projection after it was registered.

11. A medical image processing system according to claim 10, further comprising a direction-of-vision correspondence information generating unit for generating a direction-of-vision correspondence information including a correspondence established between the direction of the projection after it was registered and the direction of imaging, wherein a position of a C-arm on an angio apparatus be controlled so as to obtain a direction of imaging corresponding to the direction of the projection after it was registered and the direction-of-vision correspondence information.

12. A medical image processing system according to claim 7, wherein the direction of projection defining unit has an automatic registering unit for rotating and registering the three-dimensional projected image such that vectors of positions on a lining membrane of the blood vessel part can be placed most closely over vectors of positions on a lining membrane of the angiogram, wherein the projected image generating unit generates the three-dimensional projected image corresponding to the direction of the projection after it was registered.

13. A medical image processing system according to claim 12, further comprising a direction-of-vision correspondence information generating unit for generating a direction-of-vision correspondence information including a correspondence established between the direction of the projection after it was registered and the direction of imaging, wherein a position of a C-arm on an angio apparatus be controlled so as to obtain a direction of imaging corresponding to the direction of the projection after it was registered and the direction-of-vision correspondence information.

14. A medical image processing system according to claim 7, further comprising a blood vessel characteristic evaluating unit for evaluating a characteristic of a blood vessel, based on the three-dimensional projected image.

15. A medical image processing system according to claim 7, wherein the CT-image obtaining unit obtains the three-dimensional CT-image that a heartbeat phase is the nearest to the required angio-image of indispensability.

16. A medical image processing system comprising:
an angio-image obtaining unit for obtaining a required angio-image from multiple chronological angio-images;
an angio-image imaging direction obtaining unit for obtaining a direction of imaging as incidental information included in data on the required angio-image;
a CT-image obtaining unit for obtaining a three-dimensional CT-image corresponding to the required angio-image;
a blood vessel part extracting unit for extracting a blood vessel part in the three-dimensional CT-image;
a projected image generating unit for generating a three-dimensional projected image by projected the blood vessel part, and for generating a three-dimensional projected image corresponding to a direction of a projection after a manual operation operates the direction of the projection;
a display control unit for making display the three-dimensional projection image and the angio-image; and
a direction-of-vision correspondence information generating unit for generating a direction-of-vision correspondence information including a correspondence established between the direction of the projection after it was changed based on the manual operation and the direction of imaging,
wherein a position of a C-arm on an angio apparatus be controlled so as to obtain a direction of imaging corresponding to the direction of the projection after it was changed based on the manual operation.

17. A medical image processing system according to claim 16, wherein the three-dimensional projected image is considered to be a three-dimensional CT curved-planar projected image.

18. A medical image processing system according to claim 16, further comprising a barycenter calculating unit for calculating a barycenter of the three-dimensional projected image and a barycenter of the angiogram, and an automatic registering unit for rotating and registering the three-dimensional projected image such that the barycenter of the three-dimensional projected image and the barycenter of the angiogram can be registered, wherein the projected image generating unit generates the three-dimensional projected image corresponding to the direction of the projection after it was registered.

19. A medical image processing system according to claim 16, further comprising an automatic registering unit for rotating and registering the three-dimensional projected image such that vectors of positions on a lining membrane of the blood vessel part can be placed most closely over vectors of positions on a lining membrane of the angiogram, wherein the projected image generating unit generates the three-dimensional projected image corresponding to the direction of the projection after it was registered.

20. A medical image processing system according to claim 16, further comprising a blood vessel characteristic evaluating unit for evaluating a characteristic of a blood vessel, based on the three-dimensional projected image corresponding to the direction of the projection after it was registered based on the manual operation.

21. A medical image processing system according to claim 16, wherein the CT-image obtaining unit obtains the three-dimensional CT-image that a heartbeat phase is the nearest to the required angio-image of indispensability.

22. A medical image processing method, comprising steps of:
obtaining a required angio-image from multiple chronological angio-images;
obtaining a direction of imaging as incidental information included in data on the required angio-image;
obtaining a three-dimensional CT-image corresponding to the required angio-image;
extracting a blood vessel part in the three-dimensional CT-image;
generating a three-dimensional projected image by projecting the blood vessel part;
having display the three-dimensional projected image and the required angio-image; and
generating direction-of-vision correspondence information including a correspondence of the mutual directions of vision between a direction of a projection after it was changed and the direction of imaging.

* * * * *